United States Patent [19]
Mattson

[11] Patent Number: 4,947,412
[45] Date of Patent: Aug. 7, 1990

[54] X-RAY DETECTOR FOR CT SCANNERS

[75] Inventor: Rodney A. Mattson, Mentor, Ohio

[73] Assignee: Picker International, Inc., Highland Hts., Ohio

[21] Appl. No.: 275,782

[22] Filed: Nov. 23, 1988

Related U.S. Application Data

[63] Continuation-in-part of Ser. No. 260,403, Oct. 20, 1988.

[51] Int. Cl.$^5$ ................................................ G01T 1/24
[52] U.S. Cl. .......................................... 378/19; 378/4;
        250/368; 250/370.11; 250/370.09
[58] Field of Search ................ 378/4, 19; 250/370.08,
        250/370.09, 370.11, 368

[56] References Cited

U.S. PATENT DOCUMENTS

| | | | |
|---|---|---|---|
| 3,940,626 | 2/1976 | Hounsfield | 378/19 |
| 4,110,621 | 8/1978 | Horn | 378/19 |
| 4,145,610 | 3/1979 | Perilhou | 378/19 |
| 4,180,737 | 12/1979 | Kingsley | 378/19 |
| 4,607,164 | 8/1986 | Kubota et al. | 250/370.09 |
| 4,621,194 | 11/1986 | Yoshida et al. | 250/370.09 |

FOREIGN PATENT DOCUMENTS

| | | | |
|---|---|---|---|
| 2468999 | 5/1981 | France | 250/370.11 |
| 0244883 | 12/1985 | Japan | 250/370.11 |

Primary Examiner—Craig E. Church
Assistant Examiner—John C. Freeman
Attorney, Agent, or Firm—Fay, Sharpe, Beall, Fagan, Minnich & McKee

[57] ABSTRACT

Detectors (20) of a CT scanner (10) have a radiation receiving face (34) which is larger than a photosensitive face (30) of a photodiode (22). Lead wires (28) connect the ends of the diode photosensitive surface to terminals (26). A scintillation crystal (32) has an overhanging portion (38) which overhangs at least the interconnection between the lead wires and the photosensitive face to protect the adjoining areas of the photosensitive face from incident radiation. This enables the radiation receiving surface to be larger than the photosensitive surface. The crystal is either undercut to define the overhanging area or a section of light pipe (60) is provided between the photosensitive surface and the crystal. Increasing the radiation receiving face decreases rotor ripple artifacts. Decreasing the photosensitive face area decreases diode capacitance and increases resistance which improves amplifier performance.

10 Claims, 3 Drawing Sheets

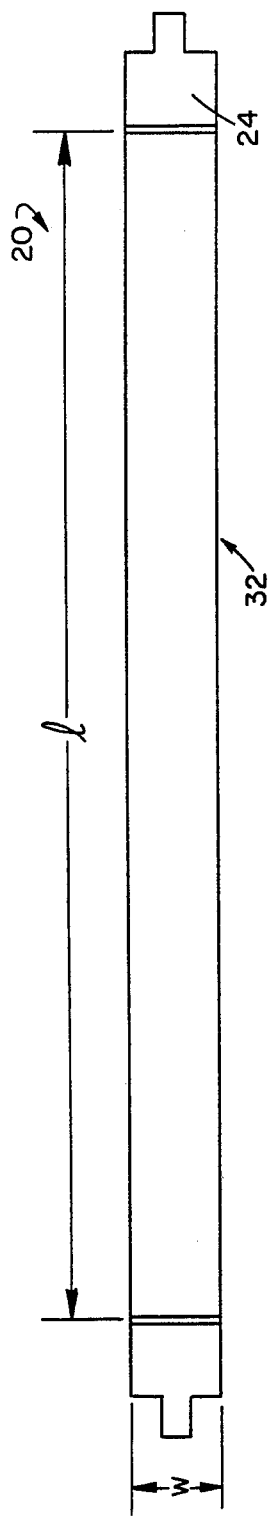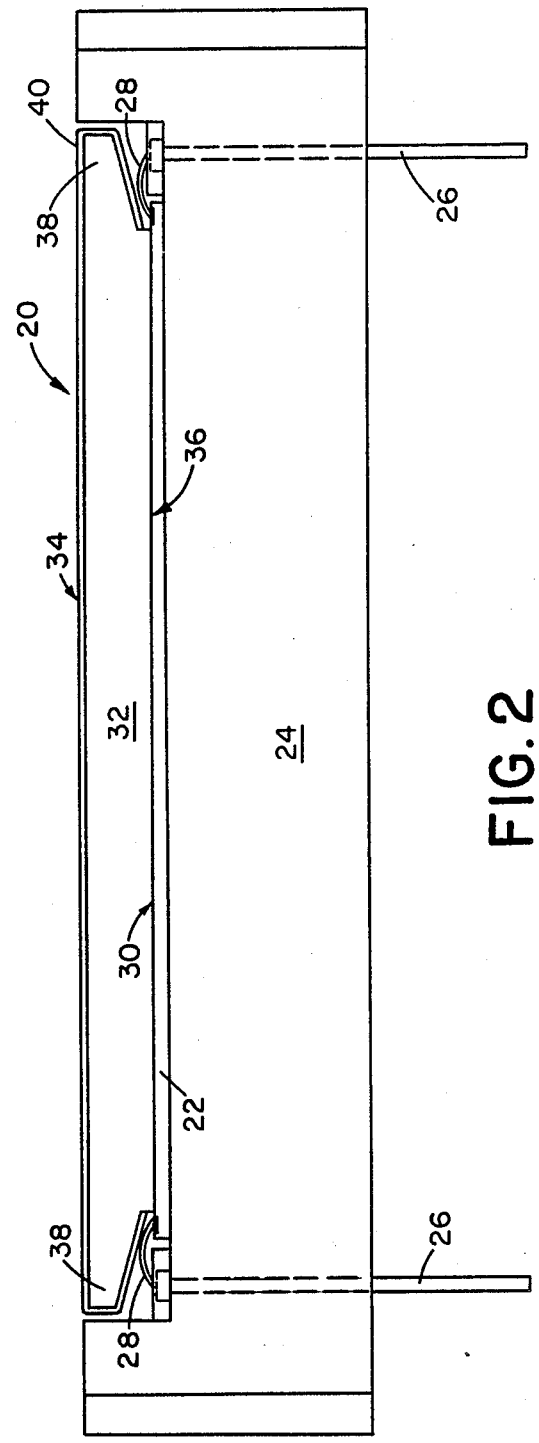

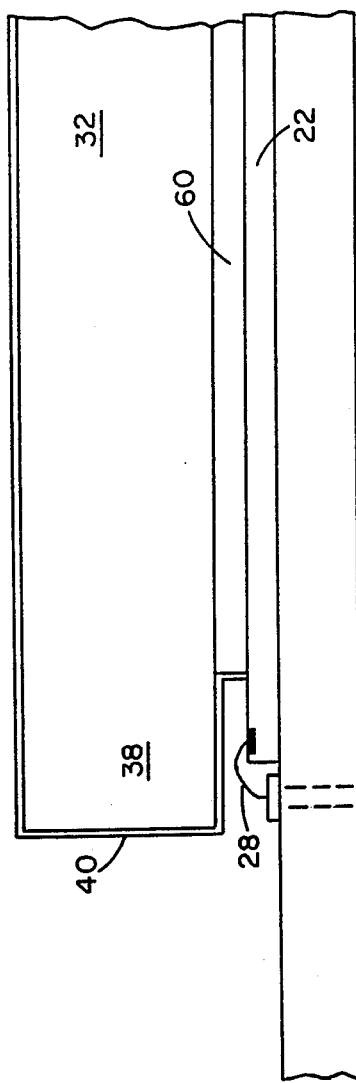
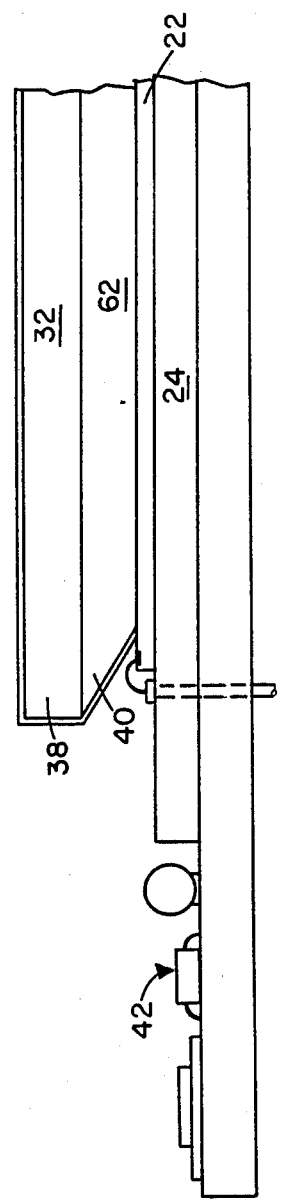
FIG. 4
FIG. 5

X-RAY DETECTOR FOR CT SCANNERS

This application is a continuation-in-part of U.S. application Ser. No. 260,403, entitled "CT Scanner with Segmented Detector Array", filed Oct. 20, 1988.

BACKGROUND OF THE INVENTION

The present invention relates to the art of radiation detection. It finds particular application in conjunction with CT scanners and will be described with reference thereto. It is to be appreciated, however, that the invention may find further application in other radiation detection devices.

In fourth generation CT scanners, a plurality of x-ray detectors have been stationarily mounted in a ring circumscribing the scan circle. X-ray energy emitted by the x-ray tube was directed to impinge upon a segment of detectors disposed on the opposite side of the scan circle. As the x-ray tube rotated around the scan circle, the irradiated portion of the stationary detector array shifted.

Typically, each detector included a scintillation crystal which converts x-ray energy into light energy. A silicon photodiode converted the light energy into an electric current. The scintillation crystal was normally a rectangular prism which is cut to match the rectangular photosensitive face of the photodiode.

Conventional photodiodes have lead wires connected to opposite ends of their photosensitive face. In order to obtain good optical coupling between the scintillation crystal and the photosensitive face, scintillation crystals terminated short of the lead wire connections. That is, the scintillation crystal has actually been smaller than the photosensitive face. This left a small length of photodiode which was not shielded by the scintillation crystal from the incident radiation. If any x-rays impinged upon the exposed photodiode surface, they tended to induce charges which migrated to the diode collector electrodes and contributed an undesirable component to the diode current.

A preamplifier amplified the photodiode current to produce a voltage signal indicative of the intensity of the radiation incident on the scintillation crystal. Of course, the performance of the CT scanner was dependent on how faithfully these components report the intensity of the incident radiation.

To optimize the results, the preamplifier should be selected such that its output is limited by the x-ray photon flux and not by electronic noise. To achieve this performance goal, preamplifier circuit designs commonly required a low capacitance and high resistance input. Because the capacitance dropped and the resistance increased as the photosensitive area of the photodiode decreased, optimal preamplifier performance called for a small photodiode.

However, other design criteria called for a large scintillation crystal, hence, large photosensitive diode face. More specifically, fourth generation scanners have been sensitive to transverse movement of the x-ray spot. The transverse focal spot movement was commonly due to wobbling of the rotating anode target, anode surface irregularities, or the like. The focal spot wobble caused corresponding periodic fluctuations in the x-ray tube output. These periodic fluctuations caused interference patterns to be superimposed on the CT image, known as "rotor ripple" artifacts. The transverse wobble of the x-ray spot tended to cause a like transverse wobble of the x-ray fan beam, shifting the beam in part off the scintillation crystals of the x-ray detectors. Elongated scintillation crystals enabled the full width of the x-ray beam to be received even during anode target wobble, hence, reduced wobble artifacts. However, elongating the scintillation crystal heretofore required elongating or enlarging the photosensitive diode face which increased its capacitance and reduced its resistance which, in turn, reduced the performance of the preamplifier. Thus, there has been a trade-off between amplifier noise signal degradation and rotor ripple signal degradation.

The present invention contemplates a new and improved detector design which overcomes the above referenced problems and others.

SUMMARY OF THE INVENTION

In accordance with one aspect of the invention, a medical diagnostic scanner is provided. A source of radiation projects radiation across an examination region to a plurality of radiation detectors. Each detector has a photodiode with a photosensitive face and a scintillation crystal. The scintillation crystal has a radiation receiving face that is larger than the photosensitive face and a second, parallel face optically coupled to the photosensitive face.

In accordance with another aspect of the present invention, an x-ray detector assembly is provided for radiographic scanners. A photodiode mounted on a substrate has a photosensitive face of a first area oriented away from the substrate. A scintillation crystal has a radiation receiving face of a second area and a second face parallel to the first. The scintillation crystal second face is optically coupled to the photosensitive face of the photodiode. In this manner, the detector is sensitive to radiation received over a larger area than the photosensitive face of the photodiode.

In accordance with a more limited aspect of the present invention, the scintillation crystal overhangs lead wire connections adjacent ends of the photosensitive face.

In accordance with another more limited aspect of the present invention, a surface of the photodiode which extends outward beyond an area of contact with the diode photosensitive area is coated with a light reflective coating. In this manner, light impinging on the scintillation crystal outside of the photosensitive area of the photodiode is reflected back into the crystal to reach the photodiode as reflecting light.

In accordance with another more limited aspect of the present invention, the scintillation crystal is larger than the photosensitive area from the diode. A light pipe interconnects the larger scintillation crystal with the smaller photosensitive face.

One advantage of the present invention is that it optimizes preamplifier performance by sizing the photodiode to meet the capacitive and shunt resistance input specifications of the preamplifier.

Another advantage of the present invention is that it reduces rotor ripple artifacts.

Another advantage of the present invention is that it increases detector x-ray capture area without degrading preamplifier performance.

Yet another advantage is that alignment of the x-ray tube and detector are less critical.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts or in various steps and arrangements of steps. The drawings are only for purposes of illustrating preferred embodiments and are not to be construed as limiting the invention.

FIG. 2 is a side view in partial section of a detector in accordance with the present invention;

FIG. 3 is a top view of the detector of FIG. 2;

FIG. 4 is an alternate embodiment of the detector of FIG. 2 having a section of light pipe between the scintillation crystal and photodiode; and, FIG. 5 is a side view in partial section on another alternate embodiment of the present invention.

DETAILED DESCRIPTION OF THE PREFERRED EMBODIMENTS

Figure 1:
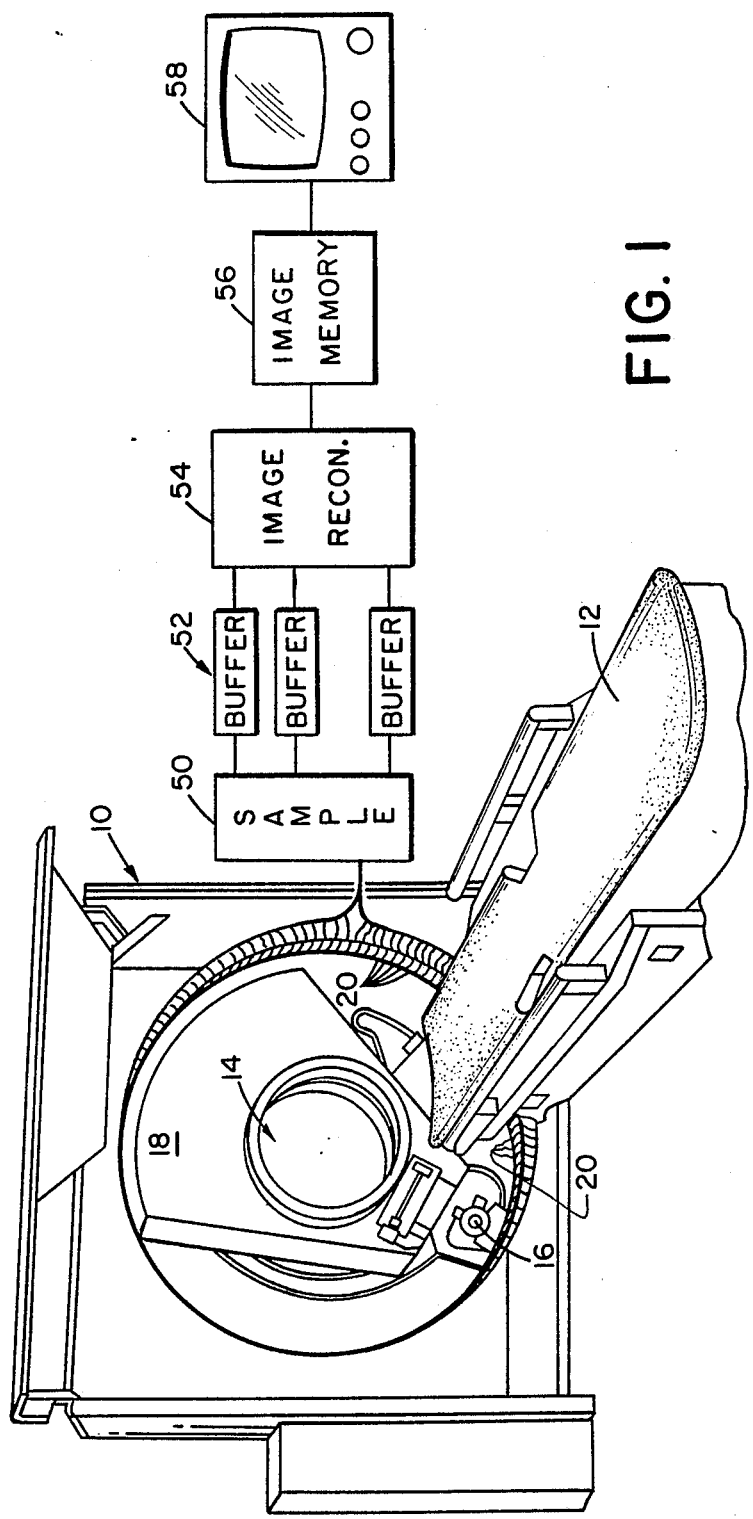
FIG. 1 is a diagrammatic illustration of a CT scanner incorporating the present invention.

With reference to FIG. 1, a CT scanner 10 is mounted in association with a patient supporting couch 12. The couch selectively moves a portion of a patient to be imaged into an examination region or scan circle 14. An x-ray tube 16 is mounted on a rotatable gantry 18 for selectively rotating a fan beam of radiation around the scan circle. A plurality of radiation detectors 20 are stationarily mounted in ring surrounding the gantry 18 and the scan circle. The x-ray tube with associated fan beam defining structures, the gantry, and the detectors are mounted such that a planar fan beam of radiation moves along detectors irradiating a contiguous arc or subset of the detectors.

With particular reference to FIGS. 2 and 3, each detector 20 includes a photodiode 22 which is supported by a substrate or mounting bracket 24. A plurality of electrical contact pins 26 extend from the substrate to plug into matching sockets in the CT scanner. Lead wires 28 interconnect the photodiode with the electrical contact pins 26.

An upper face 30 of the photodiode is photosensitive. The electrical lead wires 28 are connected with the photosensitive face 30, closely adjacent each end. A scintillation crystal 32 is optically coupled with the photodiode 22. More specifically, the scintillation crystal has an upper or radiation receiving face 34 and an oppositely disposed inner or second face 36. The second face 36 is optically coupled, such as with an optical bonding resin, to the photosensitive face of the photodiode. The radiation receiving face 34 has a greater area than the photosensitive face 30. More specifically, a portion of the scintillation crystal is under cut at each end to define overhanging crystal portions 38. Preferably, the overhanging crystal portion is relatively thick to shield the edges of the photosensitive face that extend beyond the coupling with the scintillation crystal from incident radiation.

The overhanging portion and upper surface of the scintillation crystal are coated with a light reflective substance 40, such as white paint, or the like. Incident radiation passes through the light reflective coating on the radiation receiving surface 34 and is converted into light energy by the scintillation crystal. A portion of the light travels directly to the photosensitive face of the diode and the rest of the light travels towards other surfaces of the scintillation crystal. The light reflective surfaces reflect the rest light back into the crystal. Some of the reflected light eventually travels or is reflected to the photosensitive face of the diode. By angling the lower surface of the overhanging portion 38 of the scintillation crystal, more of the light from scintillations occurring in the overhanging portion are reflected toward the central portion of the scintillation crystal to improve the chances that the light will hit or be further reflected.

To manufacture the detector, the photodiode is selected or sized to meet capacitive and shunt resistive input specifications of a preamplifier 42. The preamplifier in tandem with the photodiode is designed to provide an appropriate gain bandwidth, frequency response and noise specifications. The diode specification, such as the area of the photosensitive face, may then be adjusted, as necessary, in order to improve the performance characteristics of the amplifier. The scintillation crystal is cut to the length $l$ and width $\omega$ specifications of the CT scanner. The crystal is sized long enough to subtend the full radiation fan beam including the penumbral region associated with an x-ray tube focal spot of finite size, alignment tolerances of the x-ray tube and detector ring, and focal spot wobble. The length of the detector is also selected to be sufficiently longer than the photodiode to overhang the portion of the photodiode face at which the lead wires are connected. Material is removed from the underside of each end of the crystal to eliminate mechanical interference with the lead wires. The undercut can be a bevel, chamfer, a small rectangular step, or the like. Surfaces of the crystal, except for the diode coupling face 36 but including the undercut area, are coated with white paint or other reflective material 40. The second crystal face is optically bonded to the active area of the photosensitive face between the lead wires and the crystal, photodiodes, and substrate are epoxy bonded together.

It is to be noted that although the reflective coating on the overhanging portion reflects light back into the volume of the crystal, that light must be reflected at least once more before hitting the photodiode. Accordingly, radiation impacting the overhanging portion will produce a subdued response in the output signal.

With reference again to FIG. 1, the output signals from the amplifier associated with each photodetector are sampled by a sampling means 50. Buffer memories 52 may store the sampled data temporarily prior to image reconstruction by an image reconstructing means 54. An image memory 56 stores the reconstructed image which may be displayed on a video monitor 58, stored in computer memory or on tape, subject to further processing, or the like.

With reference to FIG. 4, the scintillation crystal 32 is again larger than the photosensitive face of the diode 22. However, rather than cutting the crystal, an optic light pipe or guide 60 is connected between the photosensitive face 30 and the crystal second face 36. The light guide extends perpendicular to the photosensitive face for a distance sufficient for the crystal lower face to clear the lead wires. Overhanging portions 38 of the crystal which extend beyond the light guide are again coated with the light reflective material 40. The exterior surface around the periphery of the light guide is also coated with the light reflective material. Alternately, the light guide may be a scintillation crystal that converts radiation passing through the upper scintillation crystal into light.

In the embodiment of FIG. 5, the scintillation crystal 32 is again larger than the photosensitive face 30 of the diode. A tapered section 62 of light transmissive material has the same upper cross section as the lower surface of the crystal and the same lower cross section as the photosensitive face. The light transmissive material may be a light guide or may be an additional piece of scintillation crystal to increase the x-ray capture capacity of the detector. The lower scintillation crystal may be the same crystalline substance as the upper scintillation crystal or may be a different scintillator, such as a scintillator with greater x-ray stopping power, one which produces light of a different spectrum, or the like.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A medical diagnostic scanner comprising:
   a source of ionizing radiation for projecting ionizing radiation across an examination region;
   a plurality of ionizing radiation detectors disposed across the examination region from the radiation source, each ionizing radiation detector including:
      a scintillation crystal having an overhanging cross portion, having a first length and a lower portion having a second length wherein the first length is longer than the second length, the scintillation crystal defining an ionizing radiation receiving face along a length of the cross portion and a second face disposed generally parallel to the ionizing radiation receiving face across the lower portion;
      a photodiode having a photosensitive face that has at least one lead wire connected adjacent one end of the photosensitive face, the photosensitive face being coupled in an optically transmissive relationship with the second face of the scintillation crystal such that the scintillation crystal cross portion is displaced from and overhangs a portion of the diode photosensitive face adjacent the lead wire.

2. The scanner as set forth in claim 1 further including a light reflective material coating at least an undersurface of the overhanging cross portion.

3. A medical diagnostic scanner comprising:
   a source of ionizing radiation for projecting ionizing radiation across an examination region;
   a plurality of ionizing radiation detectors disposed across the examination region from the radiation source, each ionizing radiation detector including:
      a scintillation crystal defining an ionizing radiation receiving face of a first length along a length of an overhanging cross portion and a second face disposed generally parallel to the ionizing radiation receiving face;
      an optic light pipe section extending between the scintillation crystal second face and a diode photosensitive face;
      a photodiode having at least one lead wire connected adjacent one end of the diode photosensitive face, the photosensitive face being coupled in an optically transmissive relationship with the optic light pipe section, the light pipe section having a second length shorter than the first length adjacent the diode photosensitive face, such that the scintillation crystal cross portion is displaced from and overhangs a portion of the diode photosensitive face adjacent the lead wire.

4. An ionizing radiation detector for CT scanners, the detector comprising:
   a supporting substrate;
   a photodiode mounted on the substrate with a photosensitive face oriented away from the substrate, the photosensitive face having a first length and lead wires connected adjacent one end of the photosensitive face;
   an optically transmissive portion having a coupling face of a second length, which second length is shorter than the first length, the optically transmissive portion being spaced from the lead wires and coupled with the photodiode photosensitive face in a light transmissive relationship;
   a scintillation crystal optically coupled with the optically transmissive portion and having an ionizing radiation receiving face of a third length, which third length is longer than the first and second lengths, the scintillation crystal being disposed with the ionizing radiation receiving face generally parallel to the photodiode photosensitive face and with a portion of the scintillation crystal spaced from and overhanging the lead wires such that the overhanging portion of the scintillation crystal shields the portion of the diode light sensitive face immediately adjacent the lead wires from ionizing radiation and defines a space therebetween;
   a light reflective coating on at least a scintillation crystal overhanging surface defined between the overhanging scintillation crystal portion and a portion of the light sensitive surface immediately adjacent the lead wires.

5. The detector as set forth in claim 4 wherein the scintillation crystal, optically transmissive portion, and the photodiode all have widths that are shorter than the first, second, and third lengths.

6. The detector as set forth in claim 4 wherein the optically transmissive portion is a section of optic light pipe.

7. The detector as set forth in claim 4 wherein the optically transmissive portion includes a scintillation crystal portion.

8. The detector as set forth in claim 4 wherein the optically transmissive portion is generally trapezoidal in cross section.

9. An x-ray detector comprising:
   a photodiode having a photosensitive face with a first area;
   lead wires connected to and extending from one end of the photosensitive face;
   a scintillation crystal for transforming received x-rays into light, the scintillation crystal having;
      a central portion which is coupled in an optically transmissive relationship to a major portion of the diode photosensitive face and optically isolated from a portion of the photosensitive face immediately contiguous to the lead wires,
      an overhanging portion which is spaced from and overhangs a portion of the diode photosensitive face connected with the lead wires to define an air gap therebetween, a radiation receiving surface disposed generally parallel to the diode photosensitive face and having a second surface area which is larger than the diode photosensitive face first surface area.

10. An ionizing radiation detector comprising:

a scintillation crystal having a rectangular ionizing radiation receiving face of length l1 and width w, the length being longer than the width;

an optically transmissive portion having a trapezoidal cross section in a plane parallel to length l1 and transverse to the ionizing radiation receiving face, the optically transmissive portion having length of substantially l1 optically coupled with the scintillation crystal and a light output face with a length l2;

a photodiode having a light sensitive face of length l3, where length l3 is longer than length l2 by a sufficient length to accommodate lead wires and shorter than l1, the scintillation crystal, optically transmissive portion, and photodiode being interconnected such that the optically transmissive portion output face is coupled in an optically transmissive relationship to the diode photosensitive face displaced from the lead wires and such that the scintillation crystal overhangs the lead wires and shields a portion of the photosensitive face adjacent the lead wires from ionizing radiation.

* * * * *